United States Patent [19]

Locsei

[11] 4,386,613
[45] Jun. 7, 1983

[54] METHOD AND APPARATUS FOR BLEEDING A TEST ANIMAL

[75] Inventor: Anthony A. Locsei, Cincinnati, Ohio

[73] Assignee: Biodec, Inc., Cincinnati, Ohio

[21] Appl. No.: 209,710

[22] Filed: Nov. 24, 1980

[51] Int. Cl.³ ............................................. A61B 17/42
[52] U.S. Cl. .................................. 128/760; 128/1 R; 604/28; 604/327
[58] Field of Search ............... 128/275, 276, 1 R, 361, 128/323, 297–301, 760, 765; 233/1 R, 26, 27; 73/436 SD; 141/34

[56] References Cited

U.S. PATENT DOCUMENTS

| 1,855,658 | 4/1932 | Whipple et al. | 128/276 |
| 1,973,990 | 9/1934 | Marrinan | 128/276 |
| 3,216,423 | 11/1965 | Blonsky et al. | 128/361 |
| 3,235,173 | 2/1966 | Unger | 233/27 |
| 3,815,579 | 6/1974 | Rose | 128/2 F |
| 3,953,172 | 4/1976 | Shapiro et al. | 23/230 R |
| 4,010,893 | 3/1977 | Smith et al. | 233/24 |
| 4,052,164 | 10/1977 | Konig | 23/259 |
| 4,093,118 | 6/1978 | Sinn et al. | 233/26 |
| 4,129,419 | 12/1978 | Hermann, Jr. | 233/1 R |
| 4,129,419 | 12/1978 | Herman, Jr. | 233/1 R |
| 4,154,793 | 5/1979 | Guigan | 422/55 |
| 4,192,250 | 3/1980 | van Duijn | 118/52 |

FOREIGN PATENT DOCUMENTS

2813724 10/1979 Fed. Rep. of Germany ...... 128/361

Primary Examiner—Richard J. Apley
Assistant Examiner—J. L. Kruter
Attorney, Agent, or Firm—Kinney & Schenk

[57] ABSTRACT

A method and apparatus for bleeding a test animal to provide a blood sample therefrom by centrifuging the test animal while being held in a predetermined position thereof to centrifuge blood from the test animal out through a bleed opening formed in a desired portion of the test animal, the centrifuged blood being collected to provide the blood sample.

14 Claims, 12 Drawing Figures

METHOD AND APPARATUS FOR BLEEDING A TEST ANIMAL

BACKGROUND OF THE INVENTION

1. Field of the Invention

This invention relates to an improved method and apparatus for bleeding a test animal to provide a blood sample therefrom as well as to improve parts of such an apparatus or the like.

2. Prior Art Statement

It is known to restrain a live test animal and extract blood therefrom to provide a blood sample that can be utilized for test purposes and the like.

One such prior known method is to extract blood from the test animal by vacuum means, such as by a hypodermic needle or by applying a vacuum to an incision area on the test animal as set forth in the U.S. Pat. No. 3,815,579 to Rose.

Other known means for extracting blood from a test animal is to milk by hand the blood from an incision cut into the test animal, such as at the tail thereof.

It is also known to mechanically restrain the test animal during the bleeding thereof and such prior known restraining means include various tubular and/or tunnel-like devices within which the test animal can be trapped with the tail extending out of one end of the same, each tubular or tunnel-like device being substantially solid from end to end except for slots provided therein adjacent the open ends to receive gate-like members to trap the animal therebetween.

Other mechanical restraining devices utilize belts or springs with screw tie-downs and other fasteners to secure the animal to a platform-like device.

Turn table-like devices for centrifuging fluids for various purposes are well known.

For example, see the centrifuging apparatus disclosed in the following seven U.S. Pat. Nos. 4,129,419—Hermann, Jr.; 4,192,250—Duijn; 4,010,893—Smith et al; 4,093,118—Sinn et al; 4,052,164—Konig; 3,953,172—Shapiro et al; and 4,154,793—Guigan.

SUMMARY OF THE INVENTION

It is a feature of this invention to provide an improved method and apparatus for bleeding a test animal to provide a blood sample therefrom.

In particular, it was found according to the teachings of this invention that a test animal could be centrifuged in such a manner that the blood sample would be centrifuged out of a bleed openings means formed in a desired portion of the test animal.

It has also been found according to the teachings of this invention that a live test animal can be so centrifuged that a suitable blood sample can be obtained therefrom without adverse effects on the test animal so that the test animal can be kept alive and be utilized for subsequent test purposes.

Accordingly, it is believed that not only does this invention provide a more humane and less traumatic method for bleeding live test animals, but also this invention provides an improved method and apparatus for bleeding a test animal to provide a blood sample that has intact cellular constitution, freshness of sample and absence of contaminants as will be readily apparent to those skilled in the pathological art, and particularly those skilled in the clinical pathological testing of blood samples from test animals.

Accordingly, one embodiment of this invention provides a method of bleeding a test animal to provide a blood sample therefrom, the method of this invention comprising the steps of holding the test animal in a predetermined position on a support means, providing a bleed opening means in a desired portion of the test animal, centrifuging the support means to centrifuge blood from the held animal out through the bleed opening means thereof, and then collecting the centrifuged blood to provide the blood sample.

Such method of this invention can be practiced by an embodiment of the apparatus of this invention that comprises a support means having means for holding the test animal in a predetermined position thereon. The apparatus has means for centrifuging the support means to centrifuge blood from the held animal out through a bleed opening means in a desired portion of the animal and the apparatus has means for collecting the centrifuged blood to provide the blood sample.

Another feature of this invention is to provide an improved holding device for holding a test animal in a desired position thereof and such holding device of this invention can be utilized with the aforementioned apparatus for bleeding a test animal or can be utilized for other purposes where it is desired to restrain a test animal in a desired position thereof.

In particular, it was found according to the teachings of this invention that a holding or restraining device for a test animal could be formed in a manner similar to a rib-cage-like construction within which the test animal could be disposed and be held in a desired position therein as the rib-cage-like construction can be made adjustable to conform to the particular contour of that test animal.

For example, one embodiment of the holding device of this invention includes a support means having a plurality of adjustable rib-like members carried thereon in two spaced apart rows thereof, each rib-like member having one end thereof pivotally mounted to the support means and another end thereof adapted to be disposed intermediate the other ends of two adjacent rib-like members disposed in the other row thereof from the row of respective rib-like member whereby the rib-like members define a tubular rib-cage-like construction within which the test animal can be disposed.

Accordingly, it is an object of this invention to provide an improved method of bleeding a test animal to provide a blood sample therefrom, the method of this invention having one or more of the novel features of this invention as set forth above or hereinafter shown or described.

Another object of this invention is to provide an improved apparatus for bleeding a test animal to provide a blood sample therefrom, the apparatus of this invention having one or more of the novel features of this invention as set forth above, or hereinafter shown or described.

Another object of this invention is to provide an improved holding device for a test animal or the like, the holding device of this invention having one or more of the novel features of this invention as set forth above or hereinafter shown or described.

Other objects, uses and advantages of this invention are apparent from a reading of this description which proceeds with reference to the accompanying drawings forming a part thereof and wherein:

DESCRIPTION OF THE PREFERRED EMBODIMENTS

While the various features of this invention are hereinafter described and illustrated as being particularly adapted to provide a method of bleeding a live test animal from the tail thereof, it is to be understood that the various features of this invention can be utilized singly or in any combination thereof to provide a means for extracting a blood sample from other parts of the live test animal as desired.

Further, it is to be understood that while the various features of this invention are hereinafter described and illustrated as being particularly adapted to provide means for bleeding test animals of the rodent family, it is to be understood that the various features of this invention can be utilized singly or in any combination thereof to provide means for bleeding test animals of other types, such as rabbits, etc.

Therefore, this invention is not to be limited to only the embodiments illustrated in the drawings, because the drawings are merely utilized to illustrate one of the wide variety of uses of this invention.

Figure 1:
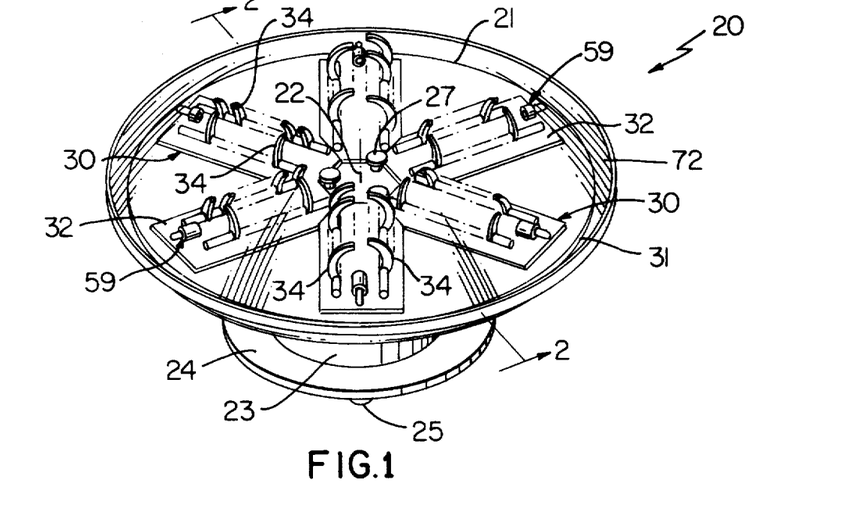
FIG. 1 is a top perspective view of the apparatus of this invention for bleeding a plurality of test animals.
Figure 2:
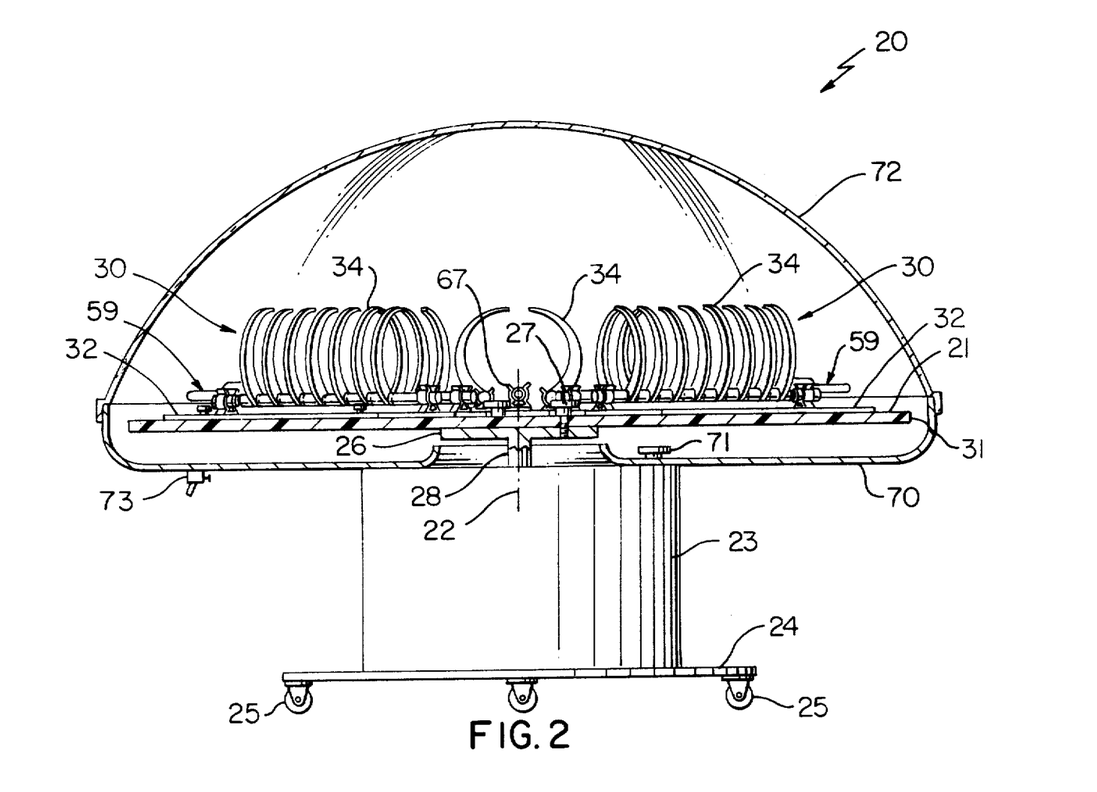
FIG. 2 is an enlarged cross-sectional view taken on line 2—2 of FIG. 1.
Figure 3:
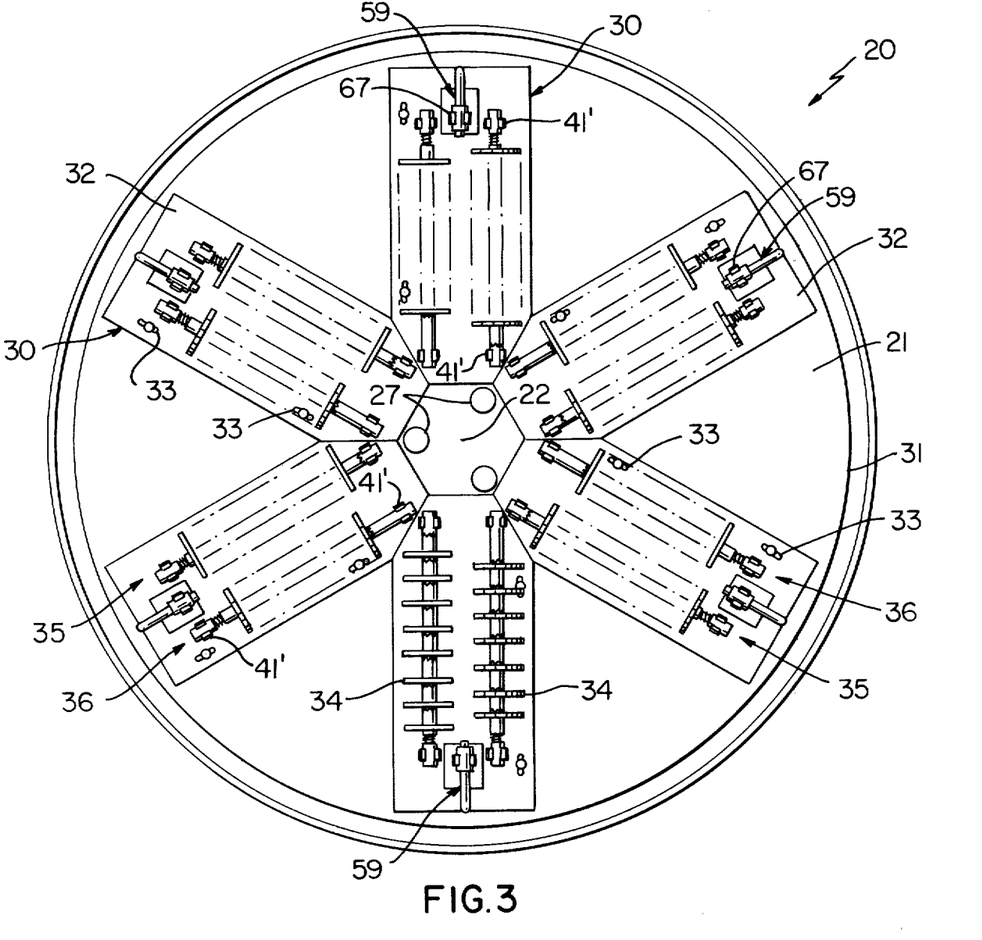
FIG. 3 is an enlarged top view of FIG. 1 with the cover member removed.

Referring now to FIGS. 1-3 of the drawings, the improved method and apparatus of this invention for bleeding a test animal to provide a blood sample therefrom is generally indicated by the reference numeral 20 and comprises a table-top-like support means 21 adapted to be rotated about its axis 22 by a suitable variable speed drive mechanism 23 supported on its support means 24 that is provided with suitable legs or caster means 25 so as to permit ease of movement of the apparatus 20 to various positions within a laboratory or the like.

The rotary table-top or support means 21 is adapted to be detachably secured to a disc-like end 26 of the rotary drive mechanism 23 by a plurality of fastening means 27 which can comprise thumbscrews or the like for quick removal.

The drive disc 26 is, in turn, carried on the rotatable drive shaft 28 of the drive mechanism 23.

While the drive mechanism 23 can comprise any suitable variable speed motor and gear train arrangement, an example of such drive mechanism 23 that has been found satisfactory according to the teachings of this invention comprises an eighth horsepower unit with a variable speed from 0 to 400 rpm and with dynamic breaking therefor.

While the rotary table 21 can comprise any suitable material, the same can comprise laminated plastic, if desired, so as to permit the same to be readily cleaned as will be apparent hereinafter.

The rotary support member 21 has a plurality of test animal holding devices of this invention detachably mounted thereon, the holding devices being generally indicated by the reference numeral 30 and being arranged on the table 21 intermediate the axis of rotation 22 thereof and the outer peripheral edge 31 thereof in a substantially balanced wheel-spoke pattern as illustrated in FIGS. 1 and 3.

While it is to be understood that other types of holding devices can be utilized with the method and apparatus 20 of this invention, it is preferred to utilize the particular holding devices 30 of this invention and the particular details of such holding device 30 will now be described.

The improved holding device 30 of this invention comprises a substantially flat support member or plate 32 that is adapted to be detachably secured to the table 21 or any other support means by suitable fastening means passing through a plurality of elongated slots 33 in order to provide for adjustment of the support 32 relative to the table 21.

For example, the fastening means for fastening the support plate 32 onto the rotary table 21 could be quick release thumbscrews similar to the thumbscrews 27 that mount the table 21 to the drive disc 26, if desired.

Figure 4:
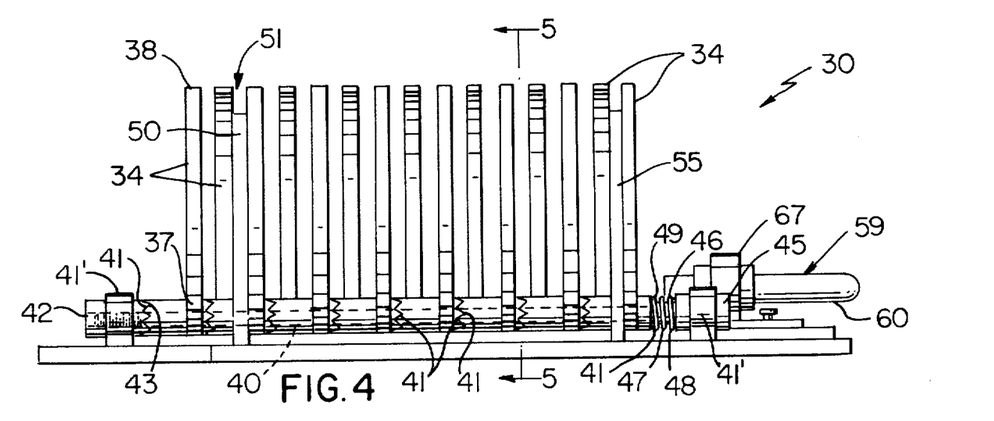
FIG. 4 is an enlarged side view of one of the holding devices of this invention that is utilized with the apparatus of FIG. 1.
Figure 5:
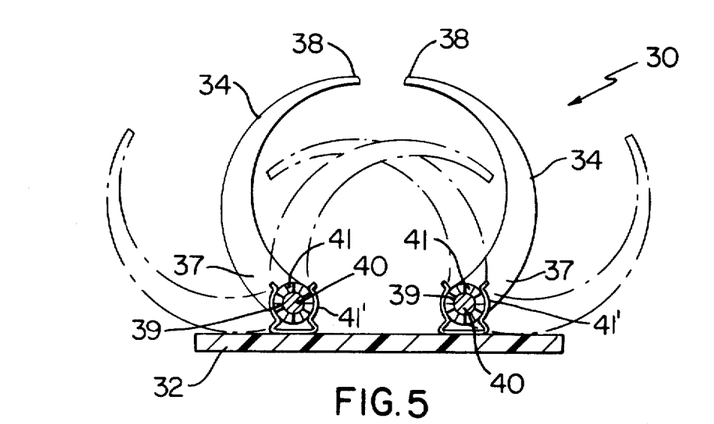
FIG. 5 is a cross-sectional view taken on line 5—5 of FIG. 4 and illustrates the ribs thereof in different positions.
Figure 6:
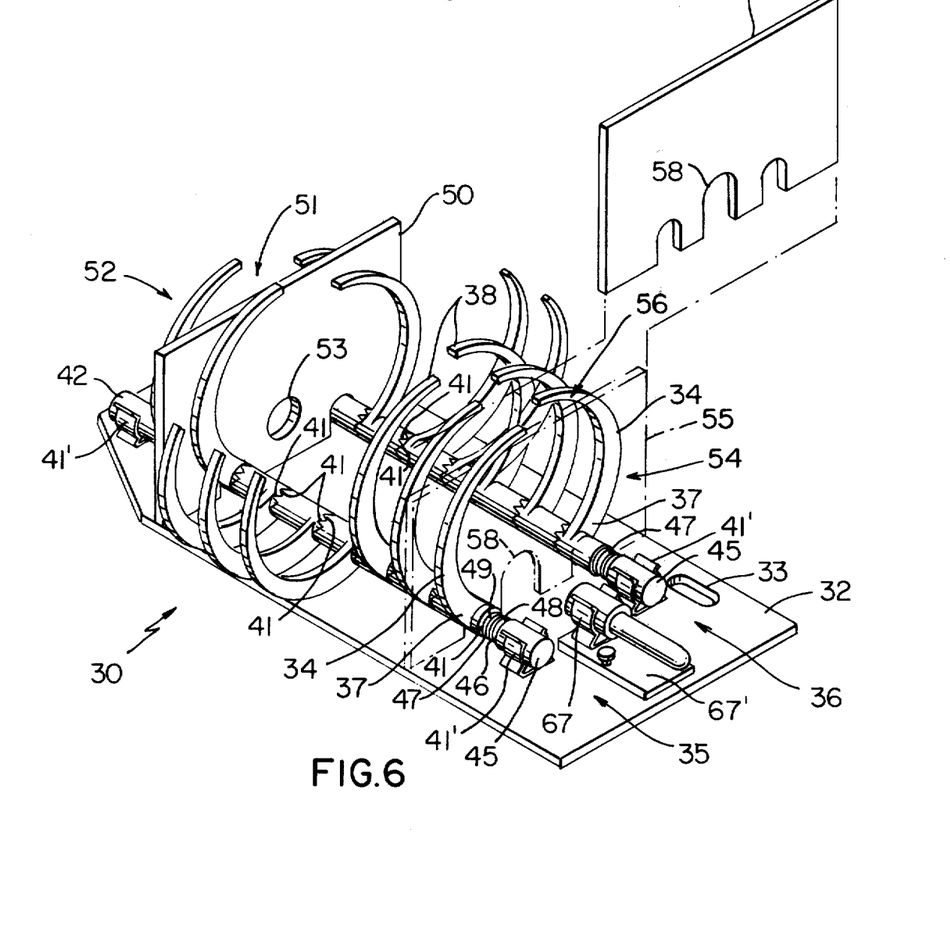
FIG. 6 is a top perspective view of the device of FIG. 4.

The holding device 30 of this invention as best illustrated in FIGS. 4-6 includes a plurality of rib-like members 34 arranged in two spaced apart rows 35 and 36 in a manner hereinafter described so that one end 37 of each rib-like member 34 is pivotally mounted to support means 32 and the other end 38 thereof is adapted to be disposed intermediate the other ends 38 of a pair of rib-like members 34 disposed in the other row from the row of the respective rib-like member 34 whereby the rib-like members 34 define a rib-cage like construction in which a test animal can be disposed in a manner hereinafter described.

The end 37 of each rib-like member 34 is substantially cylindrical and has a cylindrical opening 39 passing therethrough and adapted to be telescopically disposed on a rod-like member 40 so as to be pivotally mounted to the rod-like member 40 which, in turn, is adapted to be detachably secured to the support plate 32 by conventional spring clips 41' carried by the support plate 32 as illustrated in the drawings.

The end 37 of each rib-like member 34 has opposed faces 41 which are serrated to provide a ratchet means with the adjacent serrated face 41 of an adjacent rib-like member 34 as illustrated in the drawings whereby the ratchet faces 41 tend to rotationally lock the rib-like members 34 in each row 34 or 36 thereof in their rotational positions not only relative to each other, but also relative to the respective rod 40 for a purpose hereinafter described.

Each rod 40 has an end part 42 which is provided with a ratchet face 43 for cooperating with the ratchet face 41 of the rib-like member 34 disposed adjacent thereto.

A compression spring 47 is telescoped on each rod 40 and has its opposed ends 48 and 49 respectively bearing against the face 46 of the adjusting nut 45 and the face 41 of the rib-like member 34 disposed adjacent thereto whereby the force of the compression spring 47 tends to stack all the ends 37 of the rib-like members 34 of the particular row 35 or 36 together and against the face 43 of the end 42 of the respective rod 40 so that the serrated faces 41 and 43 tend to rotationally lock the rib-like members 34 in their selected rotational positions relative to each other and relative to the rod 40.

However, a person grabbing the end 38 of the desired rib-like member 34 can rotate the same relative to the other rib-like members 34 in the particular row 35 or 36 thereof by merely overcoming the force of the compression spring 47 to permit that the end 37 of that particular rib-like member 34 to ratchet relative to the ratchet faces 41 of the rib-like members 34 on opposite sides thereof.

Of course, the force tending to resist such rotation of the respective rib-like members 34 can be increased by further compressing the compression springs 47 by the threaded adjustment members 45. Conversely, the spring force can be reduced by backing off the threaded nuts 45 to the desired degree.

Therefore, it can be seen that each rib-like member 34 is identical to the other rib-like members 34 and the rib-like members 34 can be formed of molded plastic material while the rods 40 can be formed of stainless steel whereby the entire holding device 30 could be readily washed as a unit or in parts as desired.

Therefore, it can be seen that the holding device 30 of this invention can be formed in a relatively simple and effective manner to operate in a manner now to be described.

When it is desired to place a test animal in a particular holding device of this invention, the rib-like members 34 can be adjusted to any desired angle to define a tunnel-like rib cage construction of a diameter which will accommodate the particular test animal.

Should the test animal be a live test animal, a suitable end gate 50 can be inserted in the slot area 51 defined between the rib-like members 34 in the opposite rows 35 and 36 adjacent the end 52 of the rib cage-like construction as illustrated in FIG. 6.

It has been found that if the gate 50 has a small opening 53 passing therethrough, a live test animal, particularly one of the rodent family, when having its head end initially inserted in the other end 54 of the rib cage-like construction, will tend to run toward the gate member 50 and place its nose through the opening 53.

At the time the test animal has reached the gate 50, a rear gate 55 can be inserted into the slot area 56 disposed between adjacent rib-like members 34 of the opposite rows 35 and 36 adjacent the end 54 of the rib cage-like construction to close that end 54 whereby the test animal will be confined between the gates 50 and 55 within the rib cage-like construction.

When the test animal is of the rodent family and is to have the blood extracted from the tail thereof by the method and apparatus 20 of this invention in the manner hereinafter set forth, the rear gate 55 can have a notch 58 formed therein which will permit such tail to extend out of the end 54 of the rib cage-like construction for a purpose hereinafter described.

Figure 7:
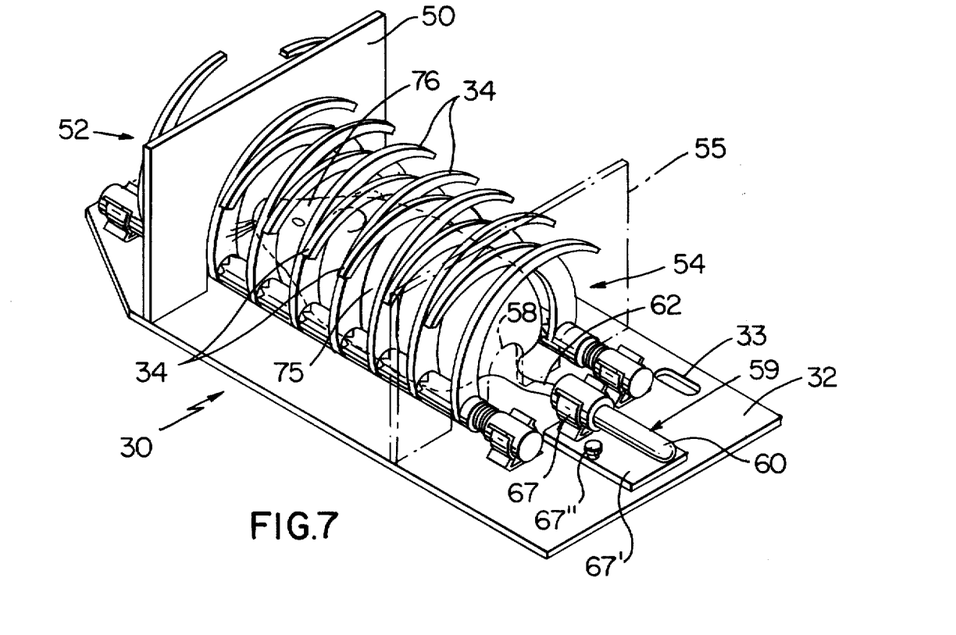
FIG. 7 is a perspective view illustrating the holding device of FIG. 4 confining a test animal therein.

Once the test animal is disposed in the holding device 30 of this invention in the manner previously described, should it be desired to prevent such test animal from substantially moving within the holding device 30, the individual rib-like members 34 can be moved relative to the other rib-like members 34 to tend to conform the rib cage-like construction to the contour of the test animal and thereby confine that test animal in a desired position within the cage-like member 30 as desired and as illustrated in FIG. 7.

Figure 8:
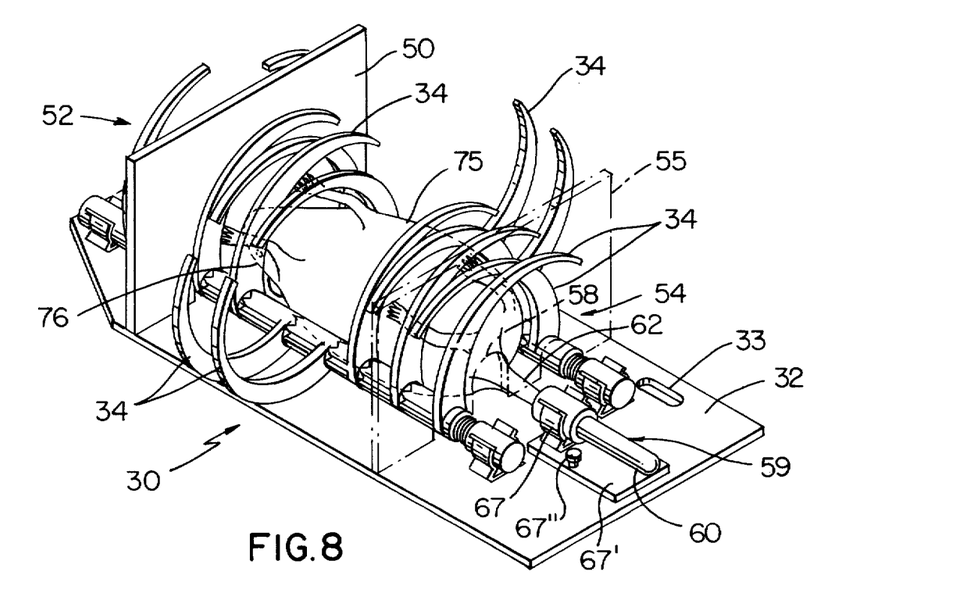
FIG. 8 is a view similar to FIG. 7 and illustrates certain ribs in an open position to expose a desired part of the test animal.

Conversely, should it be desired to expose a certain area of the test animal within the holding device 30 for surgical purposes and the like, the desired rib-like members 34 can be opened outwardly to expose a greater surface area of the test animal within the holding device 30 for such procedure as desired and as illustrated in FIG. 8.

Therefore, it can be seen that the holding device 30 of this invention readily permits a live test animal to be restrained therein and will hold that test animal within a desired position within the holding device 30 as desired. Of course, such holding device 30 can hold a dead test animal should it be desired to utilize the holding device 30 for such purpose.

As previously stated, a plurality of such holding devices 30 of this invention can be readily secured to the rotary table 21 of the apparatus 20 of this invention.

The apparatus 20 of this invention has a blood sample collecting device that is generally indicated by the reference numeral 59 for each holding device 30 so as to collect the blood sample from the test animal respectively associated with such collecting device 59.

Each collecting device 59 is for collecting a blood sample from the tail of a test animal and is particularly designed for collecting blood from the tail of a test animal from the rodent family.

Figure 9:
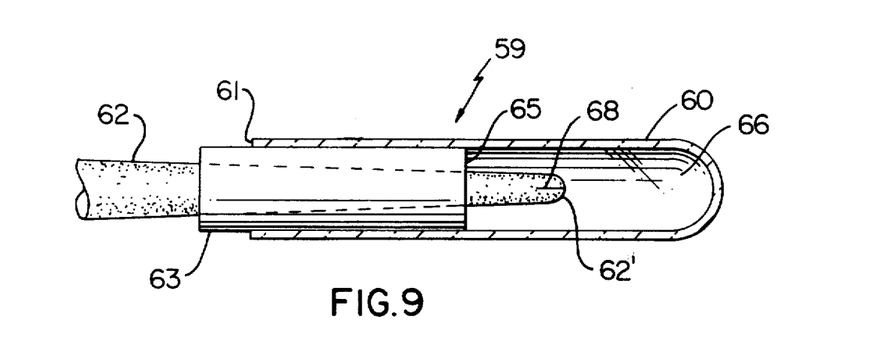
FIG. 9 is an enlarged view of part of the holding device of FIG. 4 and illustrates the test animal having its tail disposed in the blood collecting means of this invention.
Figure 10:
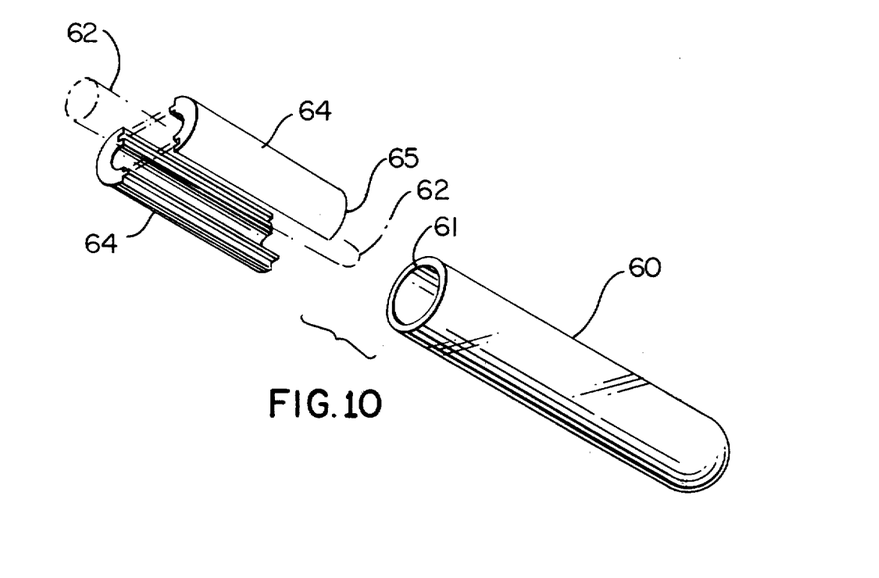
FIG. 10 is an exploded perspective view of the blood collecting means of FIG. 9.

Each collecting device 59 comprises a test tube-like receptacle 60 having its open end 61 adapted to be sealed to the tail 62 of the test animal by a sealing means 63, the sealing means 63 comprising a sleeve formed from soft rubber or the like and formed in two halves or sections 64 adapted to be respectively disposed about the tail 62 and have the open end 61 of the test tube-like member 60 inserted thereon so that the tip 62' of the tail 62 will extend beyond the end 65 of the sleeve 63 into the chamber 66 of the receptacle 60.

The degree of insertion of the receptacle 60 onto the sleeve 63 can determine the amount of blood volume that is to be extracted from the particular test animal.

For example, when the test animal is a normal sized rat, the chamber 66 can be adjusted from zero to approximately five cc with the tip 62' of the tail 62 being disposed approximately ¼ of an inch beyond the end 65 of the sleeve 63.

In order to hold each collecting device 59 to the table 51, suitable spring clips 67 can be utilized in the same manner as the spring clips 41' of the holding devices 30 previously described and such clips 67 can be carried by supports 67' that are detachably secured to respective supports 32 by fasteners 67".

However, before the receptacle 60 of the collecting device 59 is inserted onto the sleeve 63, the operator makes an incision 68 in the tip 62' of the tail 62 of the test animal by cutting the tip 62' longitudinally to provide a bleed opening means in that particular test animal to have blood extracted therefrom by the method and apparatus 20 of this invention in a manner hereinafter set forth.

In order to confine the rotary table 21 during the operation thereof hereinafter described, a stainless steel bowl 70 can be fastened to the housing of the drive mechanism 23 by suitable quick release thumb screws 71 as illustrated in FIG. 2 and such stainless steel bowl can be closed by a clear plastic dome-like removable cover 72 so that the rotary table 21 and the test animals being held in the holding devices 30 will be completely confined within the cover 72 and bowl 70 for reasons that will be apparent hereinafter. If desired, the bowl 70 can be provided with suitable drain means 73 as illustrated.

Therefore, it can be seen that the apparatus 20 of this invention can be formed in a relatively simple manner to provide means for simultaneously bleeding a plurality of live test animals in a believed-to-be humane and less traumatic manner than prior known test animal bleeding methods.

In particular, the operation of the method and apparatus 20 of this invention will now be described.

The operator loads the desired number of holding devices 30 with test animals in the manner previously described and it is preferred that a balanced arrangement of test animals be provided for the particular bleeding operation so that the table 21 will remain in balance when the same is rotated by the drive mechanism 23. Of course, it is to be understood that suitable automatically operated balancing means can be utilized with the table 21 to provide for automatic balancing thereof as desired.

In any event, the operator of the apparatus 20 can load the test animals into the holding devices 30 at the table 21 or can remove the holding devices 30 and take the same to the test animal cages as desired.

In any event, each test animal 75 is inserted into the respective holding device 30 in such a manner that the head 76 thereof will be adjacent the axis of rotation 22 of the rotary table 21 and the tail 62 will extend out toward the other periphery 31 thereof so as to be held in the sleeve 63 of the respective collecting device 59 and be cut to provide the bleed opening 68 before the receptacle 60 is slipped over the sleeve 63 in the manner illustrated in FIG. 9.

After the collecting tubes 60 have been placed over the cut tails 62 of the test animals and fastened to the table 21 by the clips 67 in the manner previously described, the operator closes the table 21 by placing the cover 72 onto the bowl 70.

Thereafter, the operator rotates the table 21 by operating the drive mechanism 23 at a predetermined speed thereof so that the rotating table 21 centrifuges the test animals in such a manner that the blood therein centrifuges out through the incisions or bleed opening means 68 in the tips 62' of the tails 62 thereof into the respective receptacles 60 to fill the chambers 66 thereof in substantially an uncontaminated manner, the time of rotation of the table 21 being approximately 10 to 15 seconds.

At this time, the rotation of the table 21 is stopped and the cover 72 is removed so that the receptacles 60 can be removed from the table 20 to have the collected blood therein immediately processed in the normal manner of testing animal blood samples.

The test animals 75 can then be removed from the holding devices 30 and returned to their cages with the only apparent adverse effect on such test animals being a numbness or dizziness caused by the rotating operation. However, it has been found that such test animals rapidly recover from such dizziness and the incisions 68 in the tails 62 thereof readily heal so that within three to four days, such test animals can again have blood samples removed therefrom in the same manner by the method and apparatus 20 of this invention as previously described.

Therefore, it can be seen that the method and apparatus of this invention readily permits test animals to be utilized over and over again in a humane and less traumatic manner than in the past to provide blood samples that are necessary in any toxic or carcenogenic testing program that normally required great quantities of test animals because of the high animal destroy rate of prior known bleeding methods.

Also, it is believed the method and apparatus of this invention permits an operator to extract such blood samples from a plurality of test animals in a more rapid manner than the prior known milking and surgical methods previously discussed.

In addition, it is believed according to the teachings of this invention that by having the head 76 of the animal 75 close to the axis of rotation 22 of the table 21, the gravity forces placed on the head area by the rotating table 21 are less than if the head 76 is out near the outer periphery 31 of the rotating table 21 whereby brain damage and the like is less likely to occur with the head 76 of the test animal 75 close to the axis of rotation 22 of the table 21.

If desired the receptacles 60 of the blood collecting devices 59 could initially have one or more chemical substances provided therein to act on or treat the blood sample that is being centrifuged out of the bleed opening means in the test animals.

For example, such chemical substance can comprise an anti-coagulant for the blood or actually be a blood coagulant, such as calcium chloride.

When calcium chloride is utilized, the same can be initially in liquid form to coat the interior walls of the receptacles 60 which then dries as a film thereon so that when the receptacles 60 are subsequently utilized in the manner previously described in the apparatus 20, the coatings on the inside surface of the receptacles 60 will act respectively on the blood samples as the same are being centrifuged from the bleed openings 68 in the manner previously described.

Of course, it is to be understood that other chemical substances can be utilized to act on the blood samples while the same are being centrifuged into the receptacles 60, as desired.

While the method and apparatus 20 of this invention has been previously described and illustrated as having the support means 67' of each blood collecting device 59 secured to the support means 32 of its respective holding device 30, it is to be understood that the collecting devices 59 can have their respective support means 67' directly secured to the rotatable table 21 if there is sufficient room between the outermost radial ends of support means 32 for their respective holding devices 30 and the outer periphery 31 of the table 21. Alternately, the respective support means 32 for the holding devices 30 could have U-shaped cutouts provided in the outermost ends thereof to accommodate the support means 67' of the respective holding devices 59 so that the support means 67' could be directly secured in an adjustable manner to the table 21.

Figure 11:
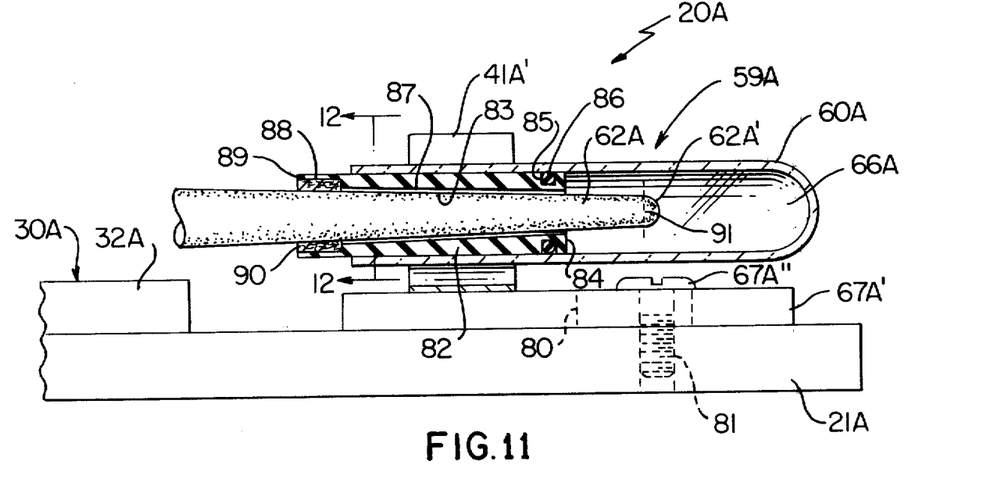
FIG. 11 is a view similar to FIG. 9 and illustrates a presently preferred tail restrainer and blood collecting means of this invention.
Figure 12:
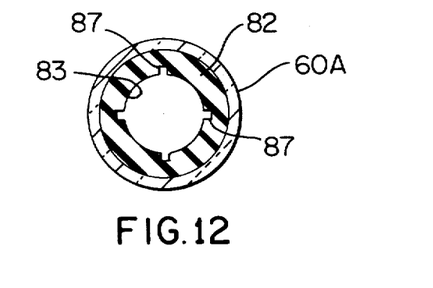
FIG. 12 is an enlarged cross-sectional view taken on line 12—12 of FIG. 11.

It has been found that certain test animals tend to bleed faster than others and therefore in order to provide blood samples from the test animals in the apparatus 20 of this invention of the same volume, a preferred embodiment for the blood collecting means is illustrated in FIGS. 11 and 12 and parts thereof similar to the apparatus 20 previously described are indicated by like reference numerals followed by the reference letter "A."

As illustrated in FIGS. 11 and 12, the method and apparatus 20A of this invention includes the rotatable support means or table 21A carrying a plurality of holding devices 30A in the manner previously described by having the support means 32A of the holding devices 30A detachably secured thereto in the manner previously described. However, the support means 67A' of the blood collecting devices 59A are directly secured to the table 21A by a plurality of fastening members 67A" respectively disposed through elongated slots 80 formed in the support means 67A' and being respectively received in threaded openings 81 in the table 21A. Of course, it is to be understood that the support means 67A' of the tail restraining or blood collecting devices 59A could be secured to the support means 32A for their respective holding devices 30A as previously described and illustrated.

In any event, it can be seen that the elongated slots 80 in the support means 67A' for the collecting devices 59A permit the same to be radially adjustable on the table 21A so as to accommodate test animals having longer or shorter tails as the case may be.

Each blood collecting device 59A includes the test tube-like receptacle 60A and a sleeve 82 having a tapered opening 83 passing therethrough to telescopically receive the tail 62A of the test animal so that the tip 62A' of the tail 62A can extend approximately one-quarter of an inch to one-half of an inch beyond the right end 84 of the sleeve 82 as illustrated in FIG. 11 while the sleeve 82 substantially seals to the tail 62A.

The sleeve 82 can be formed of rubber or rubber-like material and can comprise a one-piece member rather than two parts as provided by the sleeve 63.

In order to seal the receptacle 60A on the sleeve 82, the sleeve 82 can have an annular groove 85 adjacent the end 84 thereof carrying an O-ring seal member 86 that will seal against the inside peripheral surface of the tube 60A while permitting axial movement therebetween. In this manner, the position of the tube 60A on the sleeve 82 can be axially adjusted to vary the volume in the chamber 66A for the reasons previously set forth.

Each receptacle 60A, after being telescopically disposed on its respective sleeve 82, is adapted to be carried on its respective support means 67A' by the spring clip 41A' as previously set forth, the clip 41A' also providing for axial adjustment of the tube 60A relative to the tail 62A of its respective test animal.

As previously stated, one of the problems solved by the tail restraining and blood collecting device 59A of this invention is to permit the test animals to bleed at different rates during the centrifuging operation while substantially assuring that each resulting blood sample will be substantially of the same volume.

This feature is accomplished by having the sleeve 82 for each blood collecting device 59A provided with longitudinal air channels or grooves 87 which lead from the chamber 66A of the respective receptacle 60A to an enlarged annular counterbore 88 interrupting the end 89 of the sleeve 82 and being filled with a suitable filter material 90.

For example, the filter material 90 can comprise a chemically treated hydroscopic material to permit the blood being collected in the chamber 66A and subsequently flowing through the channels 87 to the counterbore 88 to be coagulated in the counterbore 81 and thereby prevent further bleeding from the tail 62A as a back pressure will be applied in the chamber 66A against the bleed opening even though the table is still being rotated.

Thus, it can be seen by adding a blood coagulant, such as calcium chloride, in the filter material 90, the same would stop the flow of blood through the channels 87 of the sleeve 82 so that a back pressure will be created in the chamber 66A to tend to prevent further bleeding from the tail 62A of the test animal even though the table 21A is still being rotated to centrifuge blood from other test animals that might be bleeding at a slower rate than the particular test animal which has had the blood sample thereof reach the filter 90 of its particular blood collecting device 59A. Thus, all of the resulting blood samples from a particular centrifuging operation of the apparatus 20A would substantially be of the same and desired volume.

Also, while the test animals have been previously described as having the tips 62' of the tails 62 thereof provided with longitudinal slits 68 to provide the bleed openings thereof, it has been found that the entire tip 62A' of the tail should be transversely cut off approximately one-eighth of an inch from the tail end as represented by the cut-off line 91 in FIG. 11 so as to provide a bleed opening means in the tail 62A which is believed to more readily bleed during the centrifuging operation that the previously described longitudinal slit 68.

In any event, while the operation of the apparatus 20A of this invention is substantially identical to the operation of the apparatus 20 previously described, it can be seen that the blood collecting devices 59A can each be operated to initially slip the sleeve 82 thereof over the tail 62A of the respective test animal until the tip 62A' of the tail 62A extends beyond the end 84 of the sleeve 82 a desired distance, such as one-quarter to one-half of an inch. At this time, the tail 62A is then cut at the line 91 to provide the bleed opening means. Subsequently, the receptacle 60A is slipped over the respective sleeve 82 to the desired position thereon to define the desired volume of the chamber 66A that is to receive the blood sample and then the receptacle 66A is disposed in the clip 41A to hold the same in the position illustrated in FIG. 11 during the subsequent centrifuging operation of the table 21A.

As previously stated, during the centrifuging operation when the table 21A is rotated, the blood from each tail 62A is centrifuged out of the bleed opening 91 thereof into the respective chamber 66A and as the chamber 66A begins to fill, any air trapped therein is adapted to flow out of the channels 87 and filter 90 so that no back pressure is created in the chamber 66A until the blood completely fills the same and starts flowing through the channel 87 to the filter 90. When the blood reaches the filter 90, the blood coagulant impregnated therein begins to coagulate the blood reaching the filter 90 so that the flow of blood through the channels 87 is stopped by the coagulated blood in the filter 90 so that a back pressure is now acting on the bleed opening means 91 to tend to prevent further bleeding therefrom even though the table 21A is continued to be rotated so as to make sure that the slower bleeding test animals will provide the desired volume of blood samples in the chambers 66A of their respective holding devices 59A in the manner previously described.

Therefore, it can be seen that this invention not only provides an improved method and apparatus for bleeding a test animal to provide a blood sample therefrom, but also this invention provides an improved holding device for a test animal or the like.

While the various forms and methods of this invention now preferred have been illustrated and described as required by the Patent Statute, it is to be understood that other forms and method steps can be utilized and still fall within the scope of the appended claims.

What is claimed is:

1. A method of bleeding a test animal having a tail to provide a blood sample therefrom, said method comprising the steps of holding said animal in a predetermined position on a support means, providing an open ended blood sample receptacle, providing a bleed opening in the desired tail portion of said animal, disposing tubular seal means for the open end of a blood sample receiving receptacle on said animal intermediate said bleed opening and the main body of said animal, adjusting the telescoped position of said open end of said receptacle on said tubular seal means to select a desired volume of the chamber in said receptacle beyond said tubular seal means, rotating said support means to centrifuge blood from said held animal out through said bleed opening thereof, and collecting said centrifuged blood in said chamber of said receptacle to provide said blood sample.

2. A method as set forth in claim 1 wherein said step of providing said bleed opening in a desired portion of said animal comprises the step of incising said animal.

3. A method as set forth in claim 1 wherein said step of rotating said support means comprises the step of rotating said support means about a rotational axis thereof.

4. A method as set forth in claim 3 wherein said step of holding said animal in a predetermined position on said support means comprises the step of holding said animal intermediate said axis of rotation of said support means and the outer end of said support means.

5. A method as set forth in claim 4 wherein said step of providing a bleed opening in a desired portion of said animal comprises the step of providing said bleed opening in a part of said animal that is disposed at substantially the outermost radial position from said axis of rotation of said support means.

6. A method as set forth in claim 4 wherein said step of holding said animal in a predetermined position on said support means comprises the step of holding said animal so that the head thereof is disposed proximal to said axis of rotation of said support means.

7. A method as set forth in claim 5 wherein said animal has a tail and wherein said step of holding said animal in a predetermined position on said support means comprises the step of disposing said tail of said animal substantially radially outwardly from said axis of rotation of said support means, said step of providing said bleed opening in said desired portion of said animal comprising the step of cutting an incision in substantially the tip of said tail of said animal.

8. A method as set forth in claim 1 and including the step of disposing at least one chemical substance in said chamber of said receptacle to treat said blood sample.

9. A method as set forth in claim 1 and including the steps of bleeding a plurality of test animals in the same manner and at the same time as said first-mentioned animal by holding said plurality of test animals on said support means so that said animals extend in substantially a balanced radial and wheel spoke pattern from said axis of rotation of said support means.

10. An apparatus for bleeding a test animal having a tail to provide a blood sample therefrom, said apparatus comprising support means, means for holding an animal in a predetermined position on said support means, means for rotating said support means about a rotational axis to centrifuge blood from an animal held in the predetermined position out through a bleed opening in a desired portion of said animal, and a sealable receiving receptacle means secured to said support means for collecting said centrifuged blood to provide said blood sample, said receiving receptacle means having an open end for fluid communication with the blood opening of an animal, said blood receiving receptacle means being sealingly attached to an animal so that said blood of the animal will be centrifuged into said receptacle means, said means for holding an animal in a predetermined position on said support means being adapted to hold said animal intermediate said axis of rotation of said support means and an outer end of said support means, said means for holding an animal in a predetermined position on said support means being adapted to dispose a tail of an animal substantially radially outwardly from said axis of rotation of said support means whereby an incision can be cut in substantially the tip of a tail of said animal being held to provide said bleed opening in the tail of the animal being held, said means for collecting said centrifuged blood to provide said blood sample comprising a blood receiving receptacle to be attached to a tail of an animal so that the open end of said receptacle is in substantially sealed relation over said tip of said tail whereby said blood will be centrifuged from said incision directly into said receptacle, said receptacle comprising a test tube-like member and a seal means therefor for sealing said test tube-like member in sealing relation to said tail of said animal, said seal means comprising a tubular seal means to be telescoped on said tail so that said tip of said tail will extend beyond said tubular seal means, said open end of said test tube-like member having its said open end telescoped over said seal means to seal closed said open end thereof and means for receiving said tip of said tail extend into said test tube-like member defining a chamber in said test tube-like member beyond said seal means to collect said blood sample.

11. An apparatus as set forth in claim 10 wherein said seal means has passage means therein interconnecting said chamber to the atmosphere at the exterior of said seal means.

12. An apparatus as set forth in claim 11 wherein said passage means has filter means therein.

13. An apparatus as set forth in claim 12 wherein said filter means has a blood coagulant therein to coagulate any blood flowing in said passage means from said chamber to prevent the same from reaching said exterior of said seal means.

14. A method of bleeding a test animal having a tail to provide a blood sample therefrom, comprising:
   (a) rotating a support about a rotational axis;
   (b) securing a test animal onto said support with the head of the animal being disposed proximal to said rotational axis and the tail of the animal being disposed radially outward from said rotational axis with respect to said head;

(c) cutting an incision in the tail of said test animal to provide a bleed opening therein;

(d) disposing a tubular seal means for the open end of a blood sample receiving test tube-like receptacle in a telescoped relation on said tail of said animal so as to be intermediate said bleed opening and the body of said animal;

(e) adjusting the telescoped position of said open end of said receptacle on said seal means to select a desired volume of the chamber in said receptacle beyond said seal means; and (f) collecting blood discharged from said incision in said tail in said chamber of said receptacle as said support is rotated about its rotational axis.

* * * * *